(12) United States Patent
Derchak et al.

(10) Patent No.: US 8,475,371 B2
(45) Date of Patent: Jul. 2, 2013

(54) PHYSIOLOGICAL MONITORING GARMENT

(75) Inventors: P. Alexander Derchak, Oxnard, CA (US); Larry Czapla, Coto deCaza, CA (US); Catherine Anne Rogan, Liverpool (GB)

(73) Assignee: adidas AG, Herzogenaurach (DE)

( * ) Notice: Subject to any disclaimer, the term of this patent is extended or adjusted under 35 U.S.C. 154(b) by 20 days.

(21) Appl. No.: 12/872,174

(22) Filed: Aug. 31, 2010

(65) Prior Publication Data

US 2011/0105861 A1    May 5, 2011

Related U.S. Application Data

(63) Continuation of application No. 12/869,627, filed on Aug. 26, 2010, now abandoned.

(60) Provisional application No. 61/275,633, filed on Sep. 1, 2009.

(51) Int. Cl.
*A61B 5/00* (2006.01)

(52) U.S. Cl.
USPC ........... 600/301; 600/372; 600/409; 600/529; 336/200; 324/207.15; 324/257; 327/100

(58) Field of Classification Search
None
See application file for complete search history.

(56) References Cited

U.S. PATENT DOCUMENTS

| | | | |
|---|---|---|---|
| 3,831,586 A | 8/1974 | Petit | |
| 4,033,332 A | 7/1977 | Hardway et al. | |
| 4,258,718 A | 3/1981 | Goldman | |
| 4,267,845 A | 5/1981 | Robertson, Jr. et al. | |
| 4,494,553 A * | 1/1985 | Sciarra et al. | 600/534 |
| 5,002,060 A | 3/1991 | Nedivi | |
| 5,131,399 A * | 7/1992 | Sciarra | 600/484 |
| 5,331,968 A * | 7/1994 | Williams et al. | 600/534 |

(Continued)

FOREIGN PATENT DOCUMENTS

| | | |
|---|---|---|
| WO | WO 01/28420 A1 | 4/2001 |
| WO | WO 01/76467 A2 | 10/2001 |

(Continued)

OTHER PUBLICATIONS

Tumanski, S. "Introduction coil sensors a review", Meas. Sci. Technol. 18 (2007) R31-R46.*

(Continued)

*Primary Examiner* — Bill Thomson
*Assistant Examiner* — Marie Archer
(74) *Attorney, Agent, or Firm* — Sterne, Kessler, Goldstein & Fox PLLC

(57) ABSTRACT

The present invention is directed to systems and methods for monitoring characteristics of a subject. A system according to an exemplary embodiment of the invention includes a sensor subsystem including at least one respiratory sensor disposed proximate to the subject and configured to detect a respiratory characteristic of the subject, wherein the sensor subsystem is configured to generate and transmit at least one respiratory signal representing the respiratory characteristic, and at least one physiological sensor disposed proximate to the subject and configured to detect a physiological characteristic of the subject, wherein the sensor subsystem is configured to generate and transmit at least one physiological signal representing the physiological characteristic, and a processor subsystem in communication with the sensor subsystem, the processor subsystem being configured to receive at least one of the at least one respiratory signal and the at least one physiological signal.

13 Claims, 11 Drawing Sheets

U.S. PATENT DOCUMENTS

| | | | |
|---|---|---|---|
| 5,549,113 | A | 8/1996 | Halleck et al. |
| 5,738,102 | A | 4/1998 | Lemelson |
| 5,825,293 | A | 10/1998 | Ahmed et al. |
| 5,906,004 | A | 5/1999 | Lebby et al. |
| 6,015,388 | A | 1/2000 | Sackner et al. |
| 6,047,203 | A | 4/2000 | Sackner et al. |
| 6,080,690 | A | 6/2000 | Lebby et al. |
| 6,198,394 | B1 | 3/2001 | Jacobsen et al. |
| 6,268,725 | B1 | 7/2001 | Vernon et al. |
| 6,341,504 | B1 | 1/2002 | Istook |
| 6,450,957 | B1 | 9/2002 | Yoshimi et al. |
| 6,454,719 | B1 | 9/2002 | Greenhut |
| 6,468,234 | B1 | 10/2002 | Van der Loos et al. |
| 6,517,497 | B2 | 2/2003 | Rymut et al. |
| 6,527,729 | B1 | 3/2003 | Turcott |
| 6,551,252 | B2 | 4/2003 | Sackner et al. |
| 6,599,251 | B2 | 7/2003 | Chen et al. |
| 6,600,949 | B1 | 7/2003 | Turcott |
| 6,727,197 | B1 | 4/2004 | Wilson et al. |
| 6,790,183 | B2 | 9/2004 | Murphy |
| 6,840,907 | B1 | 1/2005 | Brydon |
| 6,858,006 | B2 | 2/2005 | MacCarter et al. |
| 7,267,262 | B1 | 9/2007 | Brown |
| 7,267,652 | B2 | 9/2007 | Coyle et al. |
| 7,295,928 | B2 | 11/2007 | Hassan et al. |
| 7,395,106 | B2 * | 7/2008 | Ryu et al. ............... 600/388 |
| 7,593,767 | B1 * | 9/2009 | Modarres ............... 600/544 |
| 7,602,301 | B1 * | 10/2009 | Stirling et al. ........... 340/573.1 |
| 7,670,295 | B2 * | 3/2010 | Sackner et al. ........... 600/483 |
| 7,740,588 | B1 * | 6/2010 | Sciarra ............... 600/484 |
| 8,036,826 | B2 * | 10/2011 | MacIntosh et al. ........... 701/484 |
| 2002/0123701 | A1 | 9/2002 | Eriksen et al. |
| 2003/0094942 | A1 * | 5/2003 | Friend et al. ........... 324/244 |
| 2004/0117204 | A1 | 6/2004 | Mazar et al. |
| 2004/0122334 | A1 | 6/2004 | Yamashiro |
| 2004/0133079 | A1 | 7/2004 | Mazar et al. |
| 2004/0221847 | A1 * | 11/2004 | Berthon-Jones et al. 128/204.18 |
| 2005/0054941 | A1 | 3/2005 | Ting et al. |
| 2005/0119586 | A1 * | 6/2005 | Coyle et al. ........... 600/538 |
| 2007/0169364 | A1 | 7/2007 | Townsend et al. |
| 2008/0039700 | A1 | 2/2008 | Drinan et al. |
| 2008/0045815 | A1 | 2/2008 | Derchak et al. |
| 2008/0082018 | A1 | 4/2008 | Sackner et al. |
| 2008/0223131 | A1 | 9/2008 | Vannucci et al. |
| 2008/0269644 | A1 | 10/2008 | Ray |
| 2009/0047645 | A1 | 2/2009 | DiBenedetto et al. |
| 2009/0085706 | A1 * | 4/2009 | Baarman et al. ........... 336/200 |
| 2010/0027515 | A1 | 2/2010 | Hylton |
| 2010/0087748 | A1 * | 4/2010 | Tobola et al. ........... 600/529 |
| 2010/0292050 | A1 | 11/2010 | DiBenedetto et al. |
| 2011/0009766 | A1 | 1/2011 | McCool |
| 2011/0046499 | A1 * | 2/2011 | Klewer et al. ........... 600/534 |
| 2011/0153701 | A1 | 6/2011 | Moudgill |

FOREIGN PATENT DOCUMENTS

| | | |
|---|---|---|
| WO | WO 2006/009830 A2 | 1/2006 |
| WO | WO 2007/069111 A2 | 6/2007 |
| WO | WO 2009/074973 A1 | 6/2009 |

OTHER PUBLICATIONS

Sharp, J. T. et al; "Use of the respiratory magnetometer in diagnosis and classification of sleep apnea", Chest 1980;77;350-353.*

Rees, P.J. et al; "Use of a single pair of magnetometer coils to monitor breathing patterns in an intensive care unit"; Thorax, 1980, 35, 384-388.*

Janosek, M et al; "PCB sensors in fluxgate magnetometer with controlled excitation", Sensors and Actuators A 151 (2009) 141-144.*

Kubik, J et al; "Magnetometer with pulse excited miniature flux gate sensor", Journal of Electrical Engineering, vol. 57, No. 8/S, 2006, 80-83.*

Badler, et al., "Simulating Humans: Computer Graphics, Animation, and Control", (New York: Oxford University Press, 1993).

DeCarlo, et al., "Integrating Anatomy and Physiology for Behavior Modeling", Medicine Meets Virtual Reality 3 (San Diego, 1995).

McCool, et al., "Estimated of Ventilation From Body Surface Measurements in Unrestrained Subjects", J. Appl. Physiol., vol. 61, pp. 1114-1119 (1986).

Mead, et al., "Pulmonary Ventilation Measured from Body Surface Movements", Science, pp. 196, 1383-1384 (1967).

Paek, et al., "Postural Effects on Measurements of Tidal Volume From Body Surface Displacements", J. Appl. Physiol., vol. 68, pp. 2482-2487 (1990).

Smith et al., "Three Degree of Freedom Description of Movement of the Human Chest Wall", J. Appl. Physiol., vol. 60, pp. 928-934 (1986).

Wade, O.L., "Movements of the Thoracic Cage and Diaphragm in Respiration", J. Physiol., pp. 124-193 (1954).

Co-pending U.S. Appl. No. 12/869,578, inventors Derchak et al., filed Aug. 26, 2010.

Co-pending U.S. Appl. No. 12/869,582, inventors Derchak et al., filed Aug. 26, 2010.

Co-pending U.S. Appl. No. 12/869,576, inventor Stone, Robert, filed Aug. 26, 2010.

Co-pending U.S. Appl. No. 12/869,585, inventor Derchak, P. Alexander, filed Aug. 26, 2010.

Co-pending U.S. Appl. No. 12/869,592, inventor Derchak, P. Alexander, filed Aug. 26, 2010.

Co-pending U.S. Appl. No. 12/869,625, inventor Derchak, P. Alexander, filed Aug. 26, 2010.

Co-pending U.S. Appl. No. 12/869,586, inventor Derchak et al., filed Aug. 26, 2010.

Co-pending U.S. Appl. No. 12/836,421, inventors Powch, et al., filed Jul. 14, 2010.

* cited by examiner

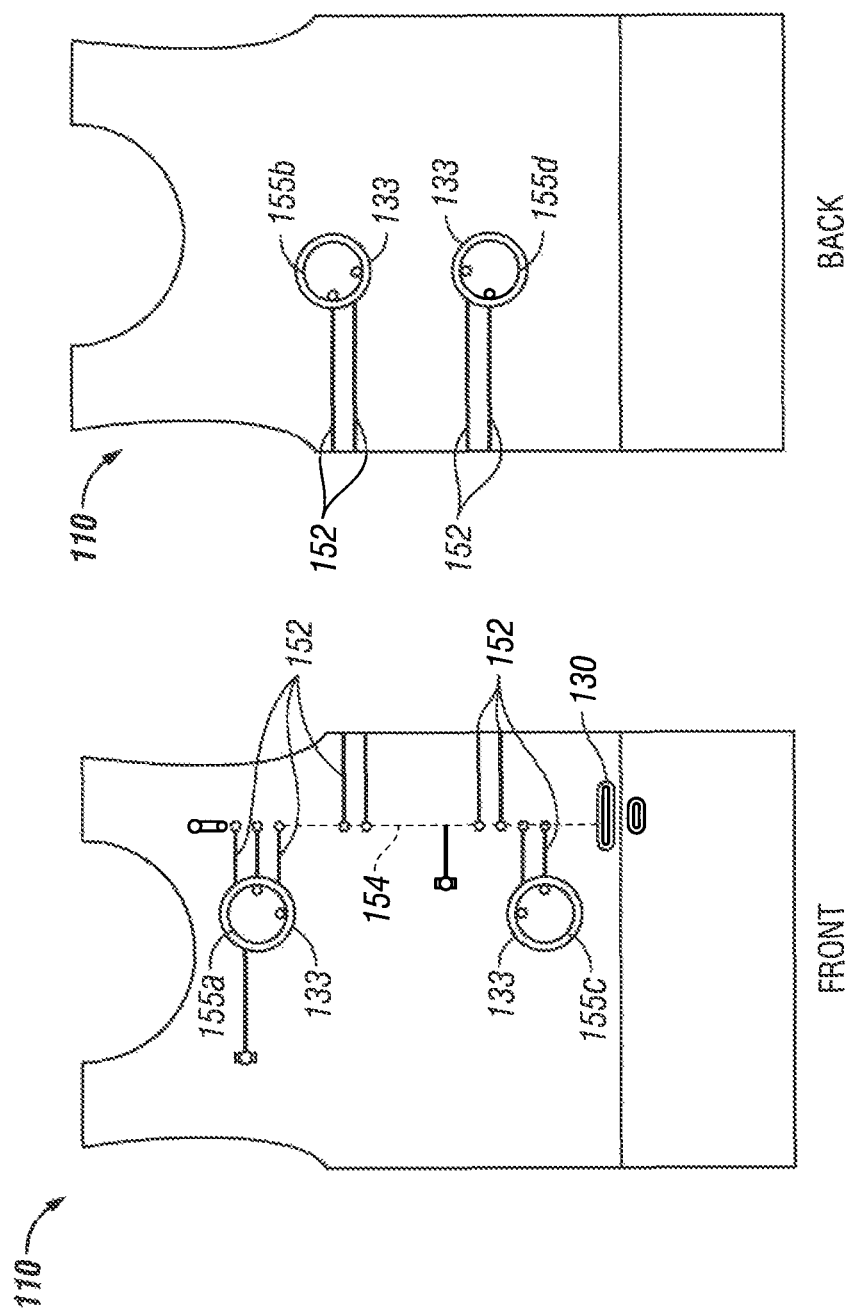

PHYSIOLOGICAL MONITORING GARMENT

CROSS-REFERENCE TO RELATED APPLICATIONS

This non-provisional application claims priority to U.S. Provisional Application No. 61/275,633, filed Sep. 1, 2009, and is a continuation application of U.S. patent application Ser. No. 12/869,627, filed Aug. 26, 2010, now abandoned each of which is incorporated herein by reference in its entirety.

FIELD OF THE INVENTION

The present invention relates generally to methods and systems for monitoring physiological and athletic performance characteristics of a subject. More particularly, the invention relates to physiological and athletic performance monitoring garments and associated systems.

BACKGROUND OF THE INVENTION

In medical diagnosis and treatment of ambulatory and non-ambulatory subjects, it is often necessary and/or desirable to monitor one or more physiological and/or athletic performance characteristics and/or parameters associated with the subject. It has also often been desirable to monitor physiological characteristics of ambulatory subjects during potentially stressful or hazardous situations, such as those often encountered by first responders (e.g., firefighters, police, emergency medical personnel, etc.) and during athletic and/or competition training.

Various systems and methods have thus been developed to monitor physiological characteristics and parameters of ambulatory and non-ambulatory subjects. Earlier physiological monitoring systems typically included electrical or electronic components (e.g., a heart rate sensor) that were fastened to wearable items or placed in pouches in the items. Individual wires between the components were then fastened to the outside of the items or disposed partially or wholly in seams and the like. Illustrative is the harness system (used in military applications) disclosed in U.S. Pat. No. 6,198,394, issued Mar. 6, 2001, which is incorporated by reference herein in its entirety.

A major problem with the earlier wearable monitoring systems or items is that the wires were wholly or partially separate from the textile material, particularly at key connection regions. As a result, the wires could, and often did, catch on or become entangled with objects, and disconnect from components.

To overcome the noted problems with the earlier systems, wearable monitoring garments having electronic circuits and data transmission lines integrated in the textile material were developed. Illustrative are the wearable monitoring garments disclosed in U.S. Pat. No. 6,080,690, issued Jun. 27, 2000, U.S. Pat. No. 5,906,004, issued May 25, 1999, U.S. Pat. No. 6,727,197, issued Apr. 27, 2004, and U.S. patent application Ser. No. 10/922,336 (Publication No. 2005/0054941 A1), filed Aug. 20, 2004, each of which is incorporated by reference herein in its entirety.

In U.S. Pat. No. 6,080,690 and U.S. Pat. No. 5,906,004, wearable monitoring garments having conductive fibers are disclosed. The noted patents provide that the conductive fibers can be disposed in a multitude of positions and orientations within the garment to facilitate connection by and between one or more sensors and a controller.

A major drawback of the disclosed garments and systems is, however, that routing of data and power between components is limited without extensive formation of electrical and data junctions in the fabric. As is well known in the art, formation of such junctions often requires a very complex and expensive manufacturing process or processes.

In U.S. Pat. No. 6,727,197 and U.S. patent application Ser. No. 10/922,336, further wearable monitoring garments are disclosed. The monitoring garments similarly include conductive fibers to facilitate connection by and between components. The disclosed garments also include integrated (and in some instances "elongate stretchable") busses for providing power to components (e.g., sensors) and for routing component signals to signal transmission or processing circuitry.

Although the disclosed garments provide an effective integrated means for routing power and data between components, there are still several drawbacks and disadvantages associated with the disclosed garments (and systems). A major drawback is that the component connections remain complex and, hence, time consuming and expensive to manufacture.

It would therefore be desirable to provide an improved physiological monitoring garment that facilitates accurate, real-time determination of a plurality of physiological characteristics and is simple to manufacture.

BRIEF SUMMARY OF THE INVENTION

In accordance with the above objects and those that will be mentioned and will become apparent below, the present invention is directed to a wearable physiological and performance monitoring garment that facilitates monitoring of physiological and performance characteristics and parameters of a subject. In a preferred embodiment of the invention, the physiological monitoring garment includes integral component connecting and data transmission means that facilitates communication by and between components employed with the garment.

In some embodiments of the invention, the physiological monitoring garment includes a magnetometer system, which is embedded in or carded by the wearable garment. In some embodiments, the physiological monitoring garment includes additional physiological sensors, such as, for example, ECG, temperature, and blood oxygen sensors, and processing and monitoring means, which similarly are embedded in or carried by the wearable monitoring garment.

BRIEF DESCRIPTION OF THE FIGURES

Further features and advantages will become apparent from the following and more particular description of the present invention, as illustrated in the accompanying drawings, in which like referenced characters generally refer to the same parts or elements throughout the views.

FIG. 12 is a front plan view of the physiological monitoring garment shown in

FIG. 11, showing a side opening thereof, according to one embodiment of the invention.

FIG. 17 is a front plan view of a physiological monitoring garment having a plurality of integral garment conductors associated therewith, according to one embodiment of the invention.

FIG. 18 is a back plan view of the physiological monitoring garment shown in FIG. 17, according to one embodiment of the invention.

DETAILED DESCRIPTION OF THE INVENTION

Figure 1:
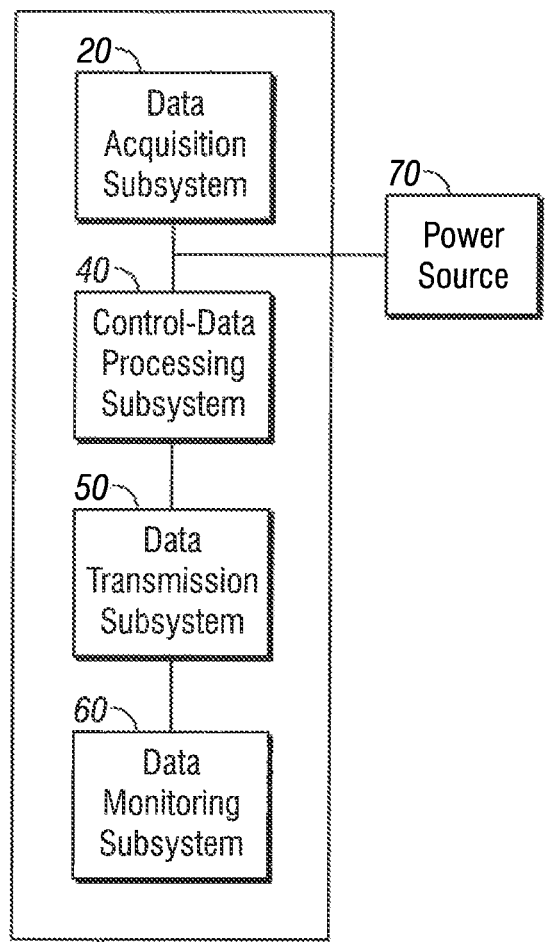
FIG. 1 is a block diagram of a physiological monitoring system, according to one embodiment of the invention.

Before describing the present invention in detail, it is to be understood that this invention is not limited to particularly exemplified garments, apparatuses, systems, circuits, or methods, as such may, of course, vary. Thus, although a number of wearable items, apparatuses, systems, and circuits similar or equivalent to those described herein can be used in the practice of the present invention, the preferred wearable items, apparatuses, systems, and circuits are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

As used in this specification and the appended claims, the singular forms "a", "an", and "the" include plural referents unless the content clearly dictates otherwise.

Further, all publications, patents, and patent applications referenced herein, whether supra or infra, are hereby incorporated by reference in their entirety.

The publications discussed herein are provided solely for their disclosure prior to the filing date of the present application. Nothing herein is to be construed as an admission that the present invention is not entitled to antedate such publication(s) by virtue of prior invention. Further, the dates of publication may be different from the actual publication dates, which may need to be independently confirmed.

Definitions

The terms "respiratory parameter" and "respiratory characteristic", as used herein, mean and include a characteristic associated with the respiratory system and functioning thereof, including, without limitation, breathing frequency (fB), tidal volume ($V_T$), inspiration volume ($V_I$), expiration volume ($V_E$), minute ventilation (VE), inspiratory breathing time, expiratory breathing time, and flow rates (e.g., rates of change in the chest wall volume). The terms "respiratory parameter" and "respiratory characteristic" further mean and include inferences regarding ventilatory mechanics from synchronous or asynchronous movements of the chest wall compartments.

According to the present invention, flow rates and respiratory accelerations can be determined from a volume signal. Further, numerous inferences regarding ventilatory mechanics can be drawn from the degree of asynchrony in movement occurring among the discrete compartments that make up the chest wall.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The terms "spatial parameter" and "spatial characteristic", as used herein, mean and include a subject's orientation and/or movement.

The term "garment", as used herein, means and includes any item that is adapted to cover at least a portion of a subject's body, including, without limitation, a shirt, vest, jacket, band, and the like.

The terms "patient" and "subject", as used herein, mean and include humans and animals.

Pulmonary ventilation, tidal volume, respiratory rate, and other associated respiratory characteristics can provide a reliable and practical measure of oxygen and carbon dioxide transpiration in a living body. Respiratory characteristics are directly connected to exercise effort, physiological stress, and other physiological characteristics. One way to externally determine tidal volume is to measure the change in thoracic volume. Change in thoracic volume is caused by the expansion and contraction of the lungs. As the gas pressure in the lungs at the maxima and minima of the pressure ranges is equilibrated to surrounding air pressure, there is a very close and monotonic relationship between the volume of the lungs and the volume of air inspired.

Accurate measurement of the change in thoracic volume involves measuring the change in the diameter of the chest at the ribcage. Measurement of the change in the diameter of the chest below the ribcage can provide additional accuracy to the measurement. Monitoring changes in the diameter of the chest below the ribcage can account for diaphragm delivered breathing where the contraction and relaxation of the diaphragm muscle causes the organs of the abdomen to be pushed down and outwards, thereby increasing the available volume of the lungs.

Monitoring and analyzing respiratory characteristics can be particularly useful in athletic applications, as there is a direct link between performance and an athlete's processing of oxygen and carbon dioxide. For example, in many athletic training situations, it is helpful to know when the athlete's body transitions between aerobic exercise and anaerobic exercise, sometimes referred to as the athlete's ventilatory threshold. Crossing over the ventilatory threshold level is an indicator of pending performance limitations during sport activities. For example, it can be beneficial for athletes to train in the anaerobic state for limited periods of time. However, for many sports, proper training requires only limited periods of anaerobic exercise interrupted by lower intensity aerobic exercises. It is difficult for an athlete to determine which state, anaerobic or aerobic, he or she is in without referencing physiological characteristics such as respiratory characteristics. Therefore, respiratory monitoring and data processing can provide substantial benefits in athletic training by allowing for accurate and substantially instantaneous measurements of the athlete's exercise state. Changes in an athlete's ventilatory threshold over time, as well as patterns of tidal volume during post-exercise recovery, can be valuable to measure improvements in the athlete's fitness level over the course of a training regime. Respiratory monitoring can further allow for monitoring and analyzing changes in a subject's resting metabolic rate.

A second ventilatory threshold exists at the point when the load on the body is such that the pulmonary ventilation is no longer sufficient to support life sustainably. Dwelling too long in this state will lead to collapse and so determination of this point can be of value in medical applications, and particularly to first responders and other emergency response personnel.

The present invention is directed to a wearable physiological monitoring garment that facilitates monitoring of physiological and performance characteristics and parameters of a subject. As indicated above, the physiological monitoring garment includes integral component connecting and data transmission means that facilitates communication by and between components employed with the garment.

In some embodiments of the invention, the physiological monitoring garment includes a magnetometer system, which is embedded in or carried by the wearable garment. As discussed in detail below, the magnetometer system facilitates accurate real-time determination of various respiratory characteristics and parameters.

In some embodiments, the physiological monitoring garment includes additional physiological sensors and processing and monitoring means, which similarly are embedded in or carried by the wearable monitoring garment. The physiological sensors can include, without limitation, sensors that are adapted to monitor and record electrical activity of the brain, heart, and other muscles (e.g., EEG, ECG, EMG), pulse rate, blood oxygen saturation level (e.g., $SpO_2$), skin temperature, and core temperature. Physiological parameters measured and/or calculated may include, for example, heart rate, respiration rate, blood oxygen level, blood flow, hydration status, calories burned, muscle fatigue, and/or body temperature.

As will readily be appreciated by one having ordinary skill in the art, the wearable physiological monitoring garment of the invention facilitates accurate, real-time determination of a plurality of respiratory and other physiological parameters and characteristics. The monitoring garment also readily accommodates ambulatory home and outpatient monitoring, and monitoring subjects during potentially stressful or hazardous situations and athletic and/or competition training.

Several embodiments of the wearable physiological monitoring garment and associated systems of the invention will now be described in detail. It is, however, to be understood that the invention is not limited to the garment(s) and systems described herein. Indeed, as will be appreciated by one having ordinary skill in the art, garments and systems similar or equivalent to the described garment and systems can also be employed within the scope of the present invention.

Physiological Monitoring System

Referring first to FIG. 1, there is shown a block diagram of an exemplary physiological monitoring system 10 that can be employed with the physiological monitoring garment of the invention. As discussed in detail below, in one embodiment of the invention, the physiological monitoring system 10 is adapted to (i) monitor and detect changes in (or displacements of) the anteroposterior diameters of the rib cage and abdomen, and axial displacement of the chest wall, and (ii) determine anatomical, physiological, and performance information associated with the monitored subject as a function of the magnetometer signals reflecting the noted anatomical displacements.

As illustrated in FIG. 1, the physiology monitoring system 10 preferably includes a data acquisition subsystem 20, a control-data processing subsystem 40, a data transmission subsystem 50, a data monitoring subsystem 60, and a power source 70, such as a battery.

In one embodiment of the invention, the data acquisition subsystem 20 includes a magnetometer system 21 having paired magnetometers that are adapted to monitor and detect changes in (or displacements of) the anteroposterior diameters of a subject's rib cage and abdomen, and axial displacement of the subject's chest wall when the magnetometers are disposed at selective anatomical subject positions. It is, however, understood that the invention is not limited to the use of paired magnetometers to measure displacements of a subject's rib cage, abdomen, and chest wall.

Although the present invention is described herein in terms of magnetometers and magnetometer systems, it is understood that other types of sensor systems capable of measuring changes in distance between two or more sensors in the system can be used in place of, or in addition to, magnetometers. Specifically, the invention is not limited to the use of electromagnetic coils or magnetometers to acquire signals representing measured changes in the anteroposterior diameters of the rib cage and abdomen, and axial displacement of the chest wall. Various additional means and devices that can be readily adapted to measure the noted anatomical parameters can be employed within the scope of the invention. Such means and devices include, without limitation, Hall effect sensors and electronic compass sensors. Wireless sensors with the capability of measuring time delay in a signal sent from one sensor to another and thereby determine the distance between the two sensors can be substituted for or provided in addition to magnetometers in accordance with the present invention.

Magnetometers (or other sensors) can be embedded in or carried by a wearable garment, such as a shirt or vest. The wearable monitoring garment eliminates the need to attach the magnetometers directly to the skin of a subject and, hence, resolves all issues related thereto. The wearable monitoring garment also facilitates repeated and convenient positioning of magnetometers at virtually any appropriate (or desired) position on a subject's torso.

According to the invention, at least one, and preferably two, magnetometers are employed to measure the noted subject parameters (or displacements). In some embodiments of the invention, two pairs of magnetometers are thus employed. In some embodiments, more than two pairs of magnetometers are employed.

Figure 2:
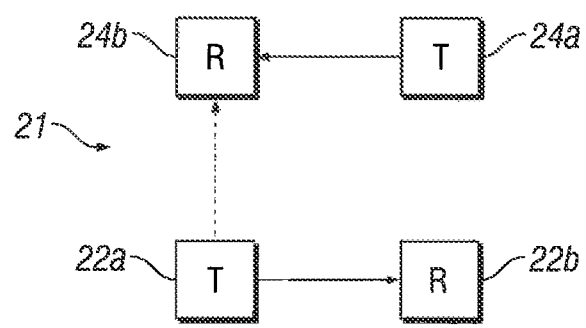
FIG. 2 is a schematic illustration of a magnetometer system, according to one embodiment of the invention.

Referring to FIG. 2, in one embodiment of the invention, magnetometer system 21 includes first transmission magnetometer 22a, first receive magnetometers 22b, second transmission magnetometer 24a, and second receive magnetometers 24b. The paired magnetometers 22a, 22b and 24a, 24b being responsive to changes in spaced distances therebetween. As discussed in detail below, first transmission magnetometer 22a is adapted to transmit a first electromagnetic field and first receive magnetometer 22b is adapted to receive the first electromagnetic field. First receive magnetometer 22b is responsive to changes in the first electromagnetic field (and, hence, the spaced distance between paired magnetometers 22a, 22b) and further adapted to generate and transmit a first signal representing a first change in the first electromagnetic field. The electromagnetic coils of embodiments of the present invention are described as "receiving" or "transmitting," however, each receiving coil can alternatively and independently be a transmitting coil, and each transmitting coil can alternatively and independently be a transmitting coil. Coils can also perform both receiving and transmitting functions.

Second transmission magnetometer 24a is adapted to transmit a second electromagnetic field and second receive magnetometer 24b is adapted to receive the second electromagnetic field. In one embodiment, second receive magnetometer 24b is responsive to changes in the first and second electromagnetic fields (and, hence, the spaced distances between paired magnetometers 24a, 24b and magnetometers 22a, 24b) and is further adapted to transmit a second signal representing a first change in the second electromagnetic field and a third signal representing a second change in the first electromagnetic field.

Referring now to FIGS. 3-7, the novel magnetometers of the invention will be described in detail. It is, however, understood that the invention is not limited to the magnetometer embodiments described herein. Indeed, as will be appreciated by one having ordinary skill in the art, various conventional magnetometers can be readily employed within the scope of the invention to monitor and/or measure anatomical distances or parameters.

Figure 3:
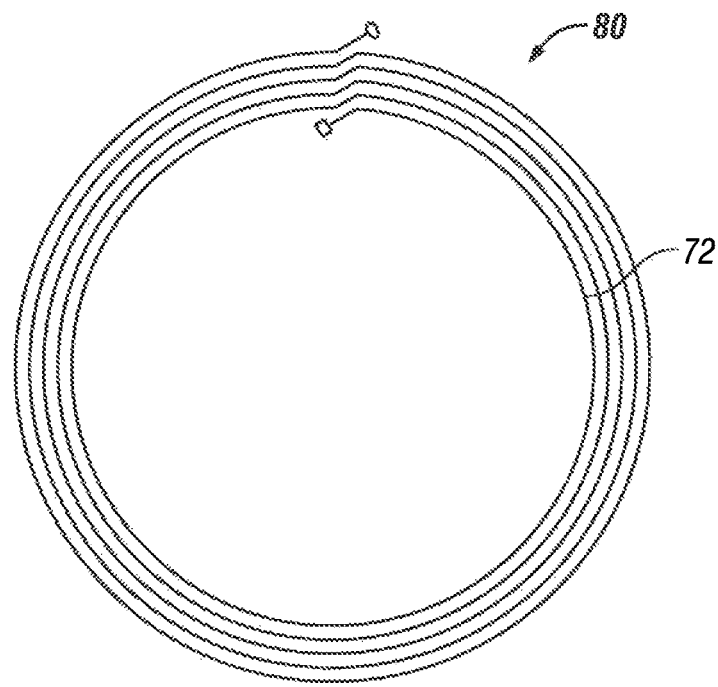
FIG. 3 is a top plan view of a magnetometer, according to one embodiment of the invention.
Figure 4:
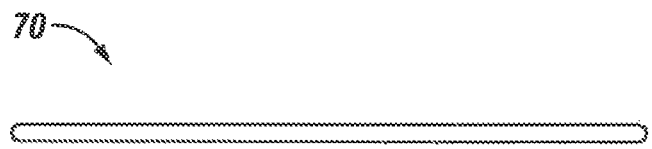
FIG. 4 is a side plan view of the magnetometer shown in FIG. 3, according to one embodiment of the invention.

Referring first to FIGS. 3 and 4, there is shown one embodiment of a low profile magnetometer 80 of the invention. In one embodiment of the invention, the magnetometer 80 comprises a multi-layer printed circuit having a conductive circular coil 72.

According to the invention, conductive coil 72 can be formed by winding the coil using standard conducting wires, such as copper, aluminum or other conductive metals, or they can be fabricated using standard multi-layer printed circuit techniques. In one embodiment, the coil is formed from 6-layer printed circuit boards with 18 turns on each layer, approximately 2 inches in diameter, with layers connected together in series using standard printed circuit layer connectors ("vias") to form a 108 turn coil.

It is understood that different sized coils can be formed in the same fashion or by winding on a thin form and adhering the coils to a flexible substrate. This coil form factor differs from previous respiratory magnetometer designs which utilize a solenoid design—a long thin coil formed around a ferromagnetic rod.

The magnetometer 80 (and associated system) preferably operates over a physical range of 10 cm to 40 cm laterally and 20 cm to 50 cm axially with the ability to measure displacement over those distances very accurately. The system noise is also extremely low, less than 10 nV/rtHz, which translates into a measurement error of 50 microns rms.

In one embodiment, power is supplied to the magnetometer 80 via a battery with a voltage range of approximately 2.8 V to 3.7 V.

Since the magnetometer circuitry is connected to coils that will be in an uncontrolled environment, all connections are preferably balanced over a very wide frequency range. Balancing all external connections minimizes electromagnetic compatibility (EMC) effects, both radiation and susceptibility, and ensure the system is extremely robust in the presence of electrostatic discharge (ESD) events. Balanced connections will also add 60 dB+reduction in rejecting AC mains parasitic pickup.

Preferably, the circuit is divided into smaller circuit blocks. The blocks can include (i) a microcontroller, (ii) analog-to-digital converter (ADC), storage, and digital signal processing (DSP), (iii) drivers, (iv) preamplifiers, and (v) input buffers. Each of the circuit blocks are discussed in detail below.

Figure 5:
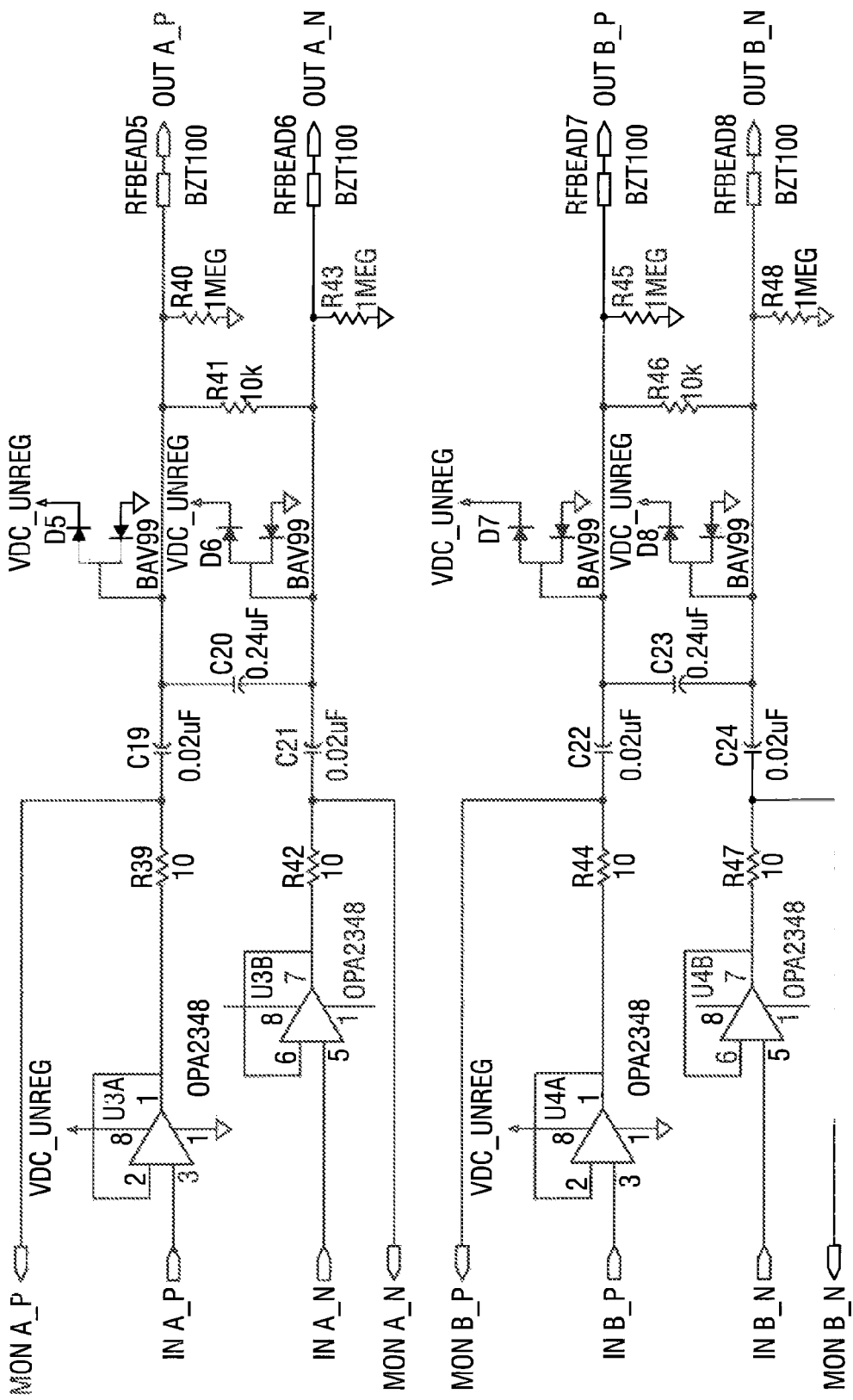
FIG. 5 is a schematic illustration of a magnetometer driver circuit, according to one embodiment of the invention.

According to the invention, the driver circuitry converts square wave drive from the microcontroller into efficient current drive for each coil and provides monitoring of the actual drive signals back to the microcontroller (see FIG. 5). The op-amps provide buffering of the microcontroller's outputs and isolation from the coils back to the microcontroller.

Since many microcontrollers have adequate current drive capability, buffering may not be required (depending on the selection of the microcontroller).

The impedance matching network of capacitors is used to match the relatively high voltage drive of the square wave to the low voltage drive requirement of the coil. This takes advantage of the Q in the circuit, enhances the fundamental frequency component of the drive, and provides isolation to the coils. Using this technique, the coils are driven with approximately 5.8 mA using only 1 mA from the power supply.

The protection diodes provide clamping to known voltages during ESD events.

Each diode has less than 1 pF capacitance. The diodes will thus not affect the normal circuit operation.

Figure 6:
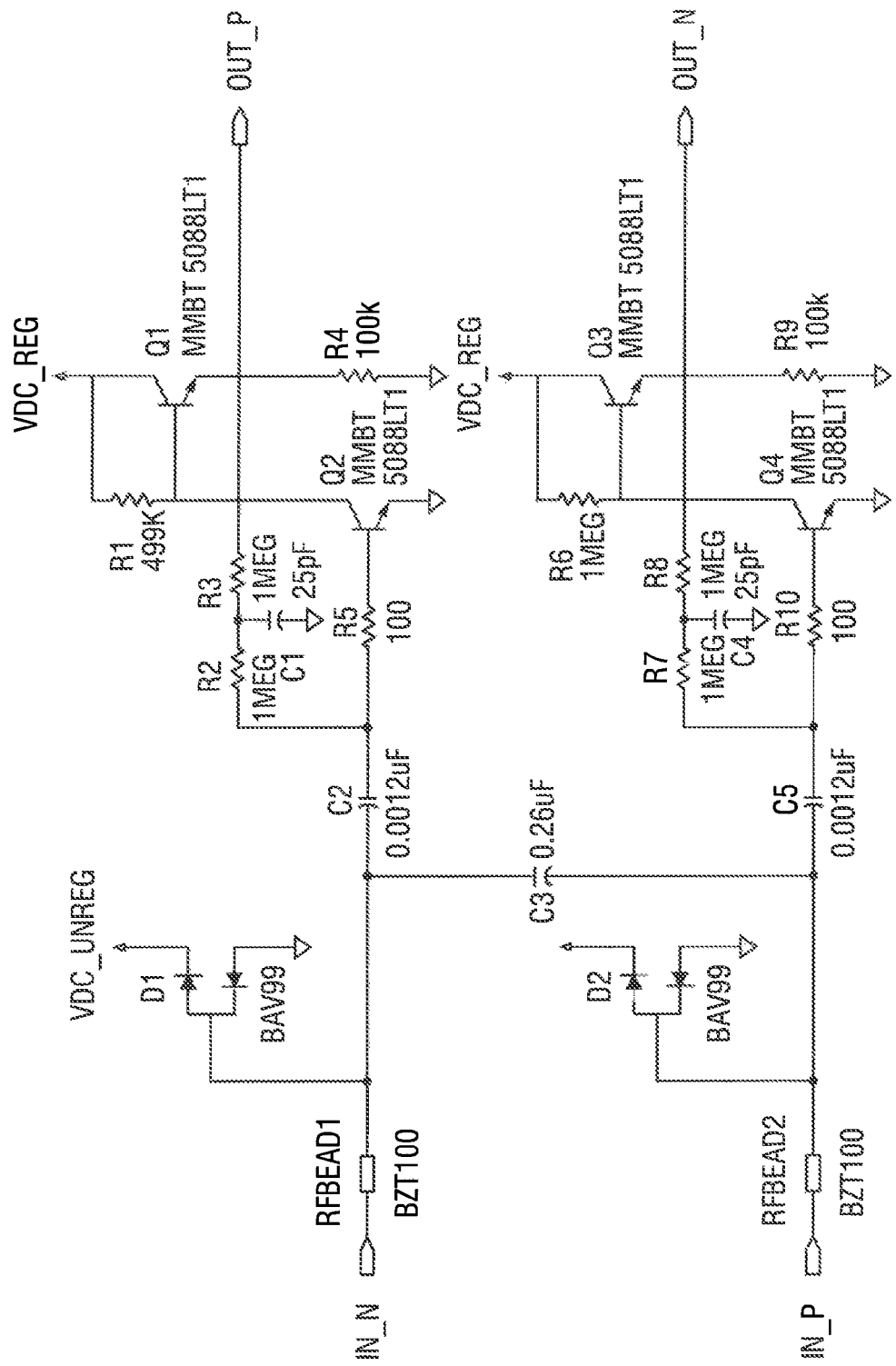
FIG. 6 is a schematic illustration of a magnetometer preamplifier circuit, according to one embodiment of the invention.

According to the invention, the preamplifier circuit provides a matching network to the coil with low-noise gain to retrieve the small signals from the coil (see FIG. 6).

In the illustrated embodiment, the preamp includes a simple two NPN transistor structure. This topology takes advantage of the low-power 2N5088 high-beta transistor to provide gain of approximately 90 at the carrier frequency. The bypass capacitors are selected to provide rejection of the mains frequency (50/60 Hz) of over 90:1. The output of the preamp is offset from ground by Vbe.

The output follower is designed and adapted to lower the output impedance of the preamp without increasing the power consumption. The voltage drop Vbe across 100 kΩ requires only 6 uA of power supply current, yet lowers the output impedance to less than 120 Ω.

Preferably, the preamp has an input noise density function of 10 nV/VHz and consumes approximately 14 uA.

The capacitor network provides matching the low impedance of the coil to the relatively high impedance of the preamp, which adds an additional gain of 4. The total gain of the preamplifier is thus 360.

Figure 7:
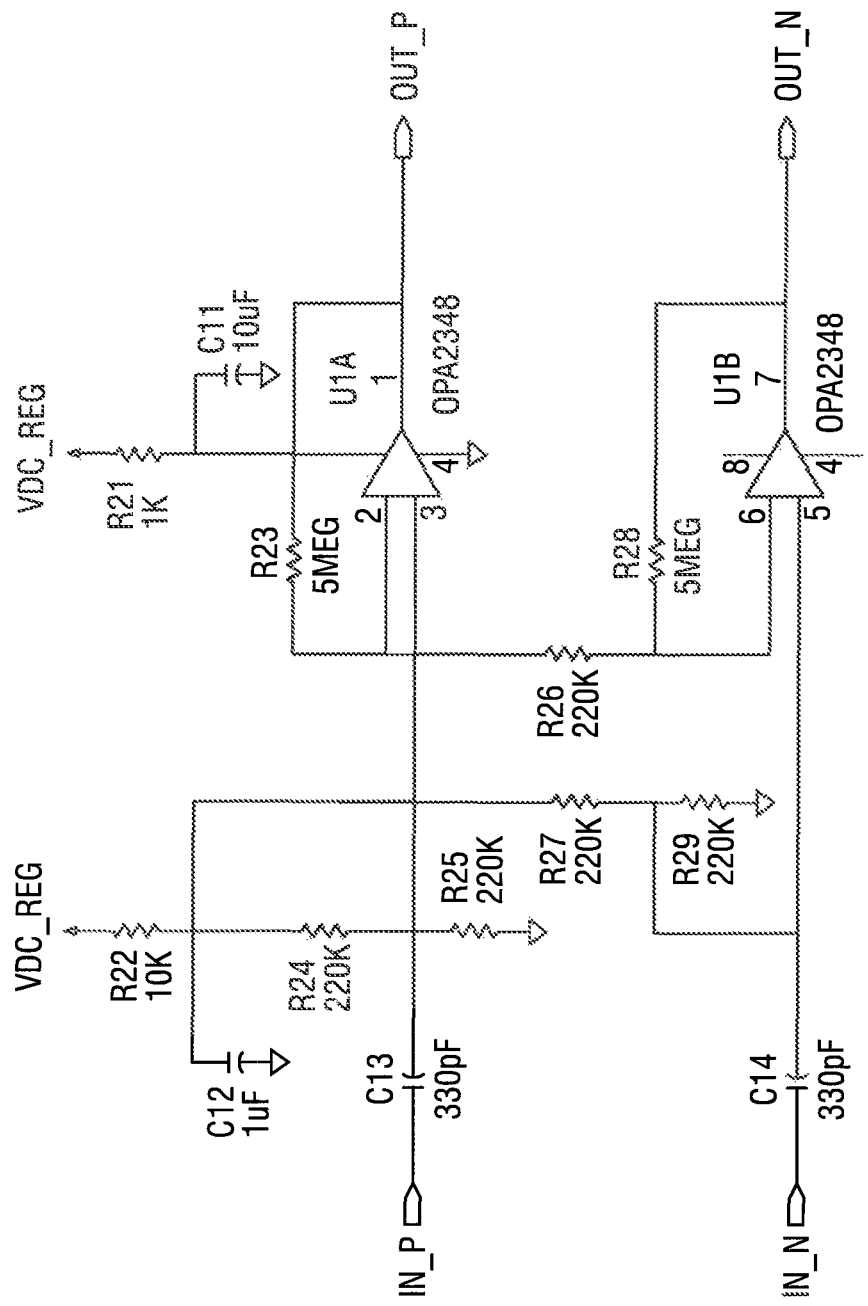
FIG. 7 is a schematic illustration of a magnetometer input buffer amplifier circuit, according to one embodiment of the invention.

According to the invention, the input buffer amplifier provides additional gain of 25, amplifying the signal enough to be digitized by the microcontroller (see FIG. 7). Since the signals from the preamp are in the range of 0.5 mV to 60 mV, it is unlikely that this stage will saturate. Op-amps may be employed since the signals would be large enough at this point to cause unacceptable distortion if simple transistor amplifiers were used.

According to the invention, various families of effective microcontroller chips can be employed within the scope of the invention. In one embodiment a TI MSF430, manufactured by Texas Instruments, microcontroller chip is employed. The noted chip is small in area and requires less than 3.5 mA of current.

The requirements of the DSP function is to provide four square waves to the drivers; one pair preferably at 8.95 kHz and the other pair preferably at 8.85 kHz. Each pair of square waves is 180 degrees out of phase.

Preferably, the microcontroller has the capability to provide 12 bit digitization of 8 channels at a rate of more than 20 kHz. Being differential, the input values are preferably processed in pairs.

In one embodiment, the eight channels are reduced to 4 values, representing TxA, TxB, Rx1, and Rx2 at each sample in time.

At the same sampling rate, four products are preferably created: TxA*Rx1, TxA*Rx2, TxB*Rx1, and TxB*Rx2. These four products are accumulated into four registers for a run length of Ss/Sps. The run length, or packet size, is therefore 400.

Preferably, every 400 accumulations the four values are retrieved, calibration factors adjust their values, and the respiration sample values are supplied to the main controller.

Referring back to FIG. 1, according to the invention, control-data processing subsystem 40 includes programs, instructions, and associated algorithms to control data acquisition subsystem 20 (and, hence, magnetometers associated therewith), data transmission subsystem 50, and monitoring subsystem 60.

Control-data processing subsystem 40 is further programmed and adapted to retrieve and process magnetometer signals reflecting changes in the magnetometer fields (and, hence, changes in spaced distances between the paired magnetometers) and to determine anatomical, physiological, and/or performance information associated with the monitored subject (as a function of the magnetometer signals), including at least one respiratory characteristic (more preferably, a plurality of respiratory characteristics). Control-data processing subsystem 40 is also referred to herein as "processor subsystem," "processing subsystem," and "data processing subsystem." The terms control-data processing subsystem, processor subsystem, processing subsystem, and data processing subsystem are used interchangeably in the present application.

Data monitoring subsystem 60 is designed and adapted to display physiological and performance characteristics and parameters generated and transmitted by control-data processing subsystem 40.

According to embodiments of the invention, data transmission subsystem 50 is programmed and adapted to monitor and control the noted communication links and, hence, transmissions by and between data acquisition subsystem 20, control-data processing subsystem 40, and data monitoring subsystem 60.

Further details of the noted physiological monitoring system are set forth in U.S. Provisional Application No. 61/275,575, filed Sep. 1, 2009, and co-pending U.S. application Ser. No. 12/869,582, filed Aug. 26, 2010, each of which is incorporated by reference herein in its entirety.

Figure 10:
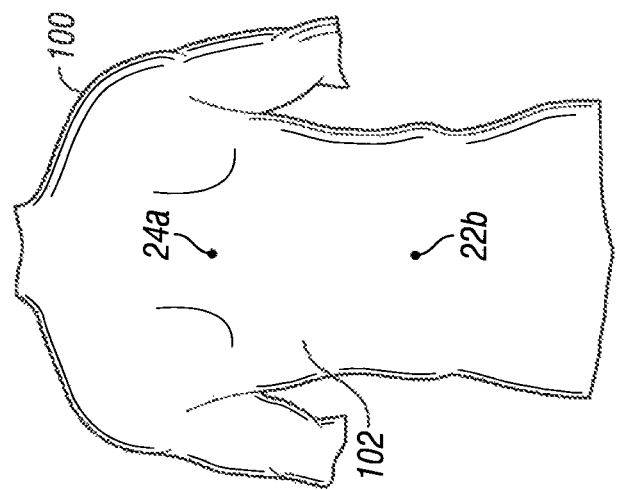
FIG. 10 is a plane view of the subject's back, showing the position of magnetometers thereon, according to one embodiment of the invention.
Figure 9:
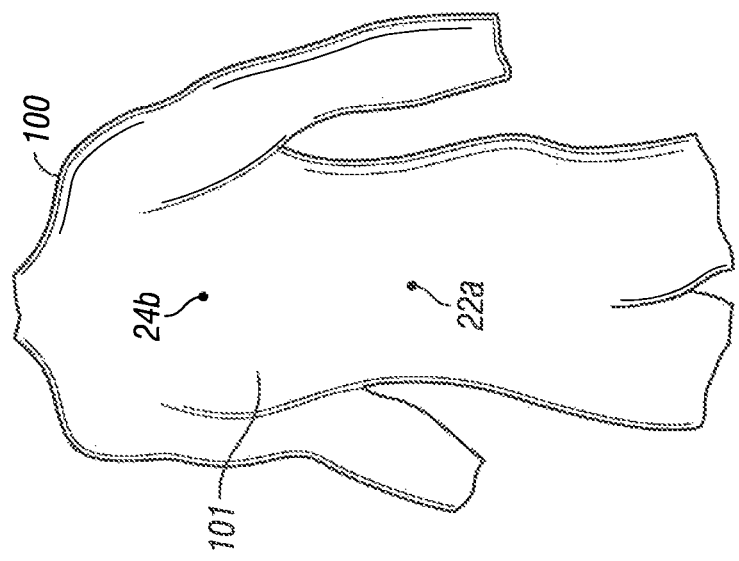
FIG. 9 is a perspective view of the subject showing the position of magnetometers on the front of the subject, according to one embodiment of the invention.
Figure 8:
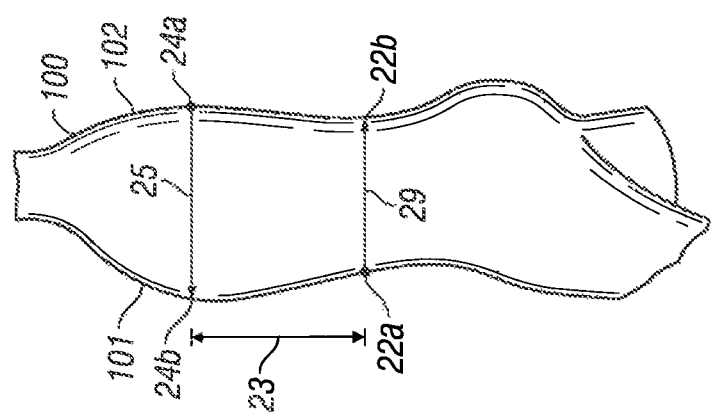
FIG. 8 is a side view of a subject, showing a position of the magnetometer system shown in FIG. 2 on the subject, according to one embodiment of the invention.

As will be readily appreciated by one having ordinary skill in the art, the magnetometers of the invention can be disposed in various anatomically appropriate positions on a subject to monitor and measure the change in distance (or displacement) between the magnetometers. Referring now to FIGS. 8-10, there is shown paired magnetometers 22a, 22b, 24a, 24b positioned on a subject or patient 100, in accordance with the inventions disclosed in the above referenced U.S. Provisional Application No. 61/275,575, U.S. application Ser. No. 12/869,582, and co-Pending U.S. application Ser. No. 12/231,692, which is similarly incorporated by reference herein in its entirety.

As illustrated in FIGS. 8-10, the first transmission magnetometer (i.e., first transmitter) 22a is preferably positioned on front 101 of subject 100 proximate the umbilicus of subject 100, and the first receive magnetometer (i.e., first receiver) 22b is preferably positioned proximate the same axial position, but on back 102 of the subject 100. Second receive magnetometer (i.e., second receiver) 24b is preferably positioned on front 101 of subject 100 proximate the base of the sternum and second transmission magnetometer (i.e. second transmitter) 24a is positioned proximate the same axial position, but on back 102 of subject 100.

As subject or patient 100 breathes, displacement(s) of the rib cage and abdomen (i.e., changes in the distance between each pair of coils 22a, 22b and 24a, 24b, denoted, respectively, by arrow 29 and arrow 25), is determined from measured changes in voltage between paired coils 22a, 22b and 24a, 24b. The axial displacement of the chest wall, denoted by arrow 23, (e.g., xiphi-umbilical distance (Xi)), is also determined from measured changes in voltage between transmission coil 22a and receive coil 24b. In this embodiment magnetometer 24b is a dual-function electromagnetic coil, where "dual function coil" refers to a coil capable of receiving transmissions from a plurality of different transmission coils (i.e., magnetometer 24b is adapted to receive magnetic field transmissions from magnetometers 22a and 24a).

As indicated above, the measured displacements are typically employed to determine anatomical and physiological information associated with the monitored subject 100, including at least one respiratory characteristic. As set forth in U.S. Provisional Application No. 61/275,575, filed Sep. 1, 2009, and co-pending U.S. application Ser. No. 12/869,582, additional paired magnetometers can also be employed, and the multiple measured displacements can be employed to assess additional anatomical, physiological, and performance characteristics, such as determining and characterizing the relationship(s) of chest wall movement(s) to respiratory activity and respiratory associated events such as speaking, sneezing, laughing, and coughing.

As also set forth in U.S. Provisional Application No. 61/275,575, filed Sep. 1, 2009, and co-pending U.S. application Ser. No. 12/869,582, data acquisition subsystem 20 can additionally include at least one additional physiological sensor (preferably, a plurality of additional physiological sensors) adapted to monitor and record one or more physiological characteristics associated with monitored subject 100. The physiological sensors can include, without limitation, sensors that are adapted to monitor and record electrical activity of the brain, heart, and other muscles (e.g., EEG, ECG, EMG), pulse rate, blood oxygen saturation level (e.g., $SpO_2$), skin temperature, and core temperature. Physiological parameters measured and/or calculated may include, for example, heart rate, respiration rate, blood oxygen level, blood flow, hydration status, calories burned, muscle fatigue, and/or body temperature.

Exemplary physiological sensors (and associated systems) are disclosed in U.S. Pat. No. 6,551,252, issued Apr. 22, 2003, U.S. Pat. No. 7,267,652, issued Sep. 11, 2007, co-pending U.S. patent application Ser. No. 11/764,527, filed Jun. 18, 2007, and International Application No. PCT/US2005/021433, each of which is incorporated by reference herein in its entirety.

Data acquisition subsystem 20 can also include one or more audio sensors, such as, for example, a microphone, for monitoring sounds generated by a monitored subject, and a speaker to enable two-way communication by and between the monitored subject and a monitoring station or individual.

In some embodiments of the invention, the data acquisition subsystem 20 can include means for directly monitoring the subject's orientation and/or movement, e.g., spatial parameters. According to the invention, various conventional means can be employed to monitor or measure subject orientation and movement, including optical encoders, proximity and Hall effect switches, laser interferometry, accelerometers, gyroscopes, and/or global positioning systems (GPS).

In one embodiment, the means for directly monitoring the orientation and movement of a subject includes at least one multi-function inertial sensor (e.g., 3-axis accelerometer or 3-axis gyroscope). As is well known in the art, orientation and motion of a subject can be readily determined from the signals or data transmitted by a multi-function inertial sensor.

Physiological Monitoring Garment

As indicated above, the physiological monitoring garment of the invention includes a wearable garment that is configured and adapted to cooperate with the aforementioned physiological monitoring system. The physiological monitoring garment can thus include paired magnetometers, such as paired magnetometers 22a, 22b, 24a, 24b, discussed above and/or one or more physiological sensors and associated processors, control units and circuits. The physiological sensors can include, without limitation, sensors that are adapted to monitor and record electrical activity of the brain, heart, and other muscles (e.g., EEG, ECG, EMG), pulse rate, blood oxygen saturation level (e.g., $SpO_2$), skin temperature, and core temperature. Physiological parameters measured and/or calculated may include, for example, heart rate, respiration rate, blood oxygen level, blood flow, hydration status, calories burned, muscle fatigue, and/or body temperature.

According to the invention, the physiological monitoring garment can include various garments or items that are adapted to cover at least a portion of a subject's body, such as a shirt, vest, jacket, band, and the like. It is thus to be understood that, although the monitoring garment describe below includes a vest, the invention is not limited to the described garment.

Figure 12:
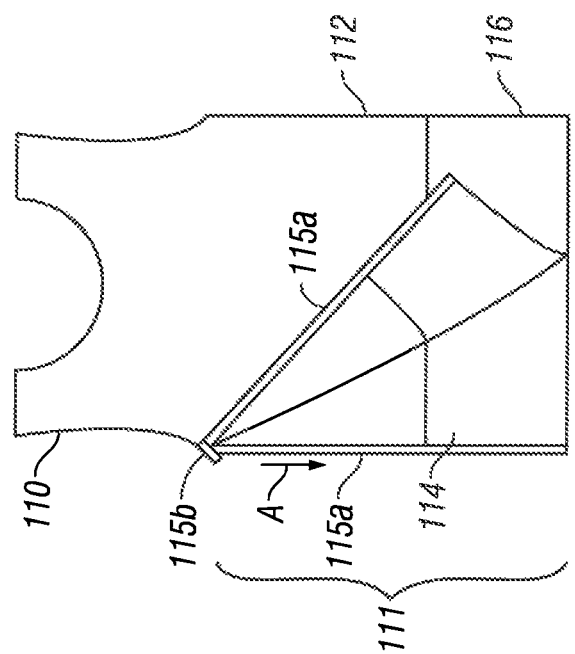
Figure 11:
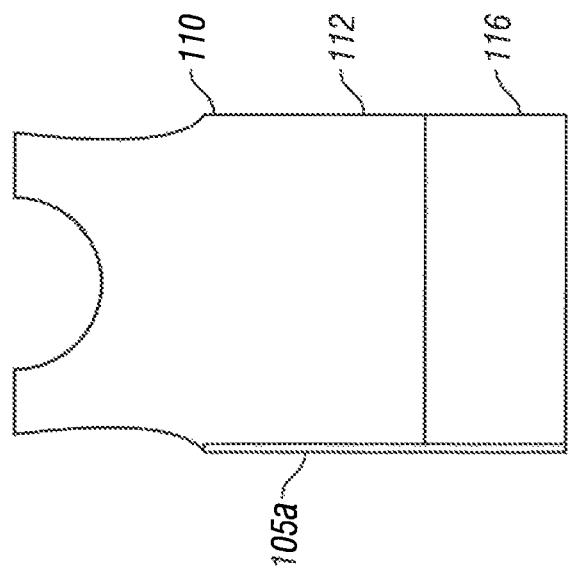
FIG. 11 is a front plan view of a physiological monitoring garment, according to one embodiment of the invention.
Figure 13:
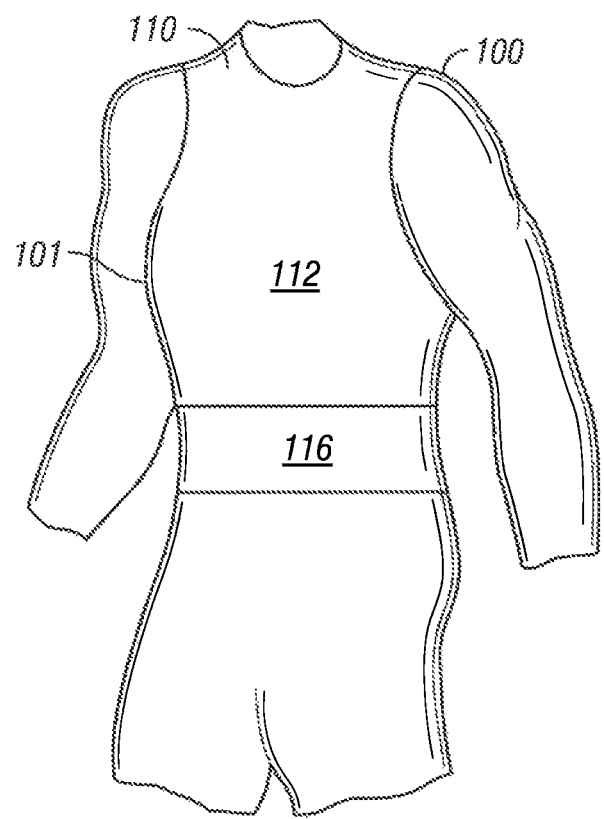
FIG. 13 is a front perspective view of a subject wearing the physiological monitoring garment shown in FIGS. 11 and 12, according to one embodiment of the invention.

Referring now to FIGS. 11-13, there is shown one embodiment of a physiological monitoring garment 110 of the invention. As illustrated in FIG. 13, the monitoring garment 110 preferably includes a body conforming garment (in this instance, a body conforming sleeveless shirt or vest).

The physiological monitoring garment or vest 110 preferably includes a front panel or section 112 and a rear panel or section 114, having an opening 111 that is preferably disposed on one side of vest 110. In the illustrated embodiment, vest 110 further includes a bottom panel or section 116.

As illustrated in FIG. 12, front panel 112 and rear panel 114 include cooperating closure means 115a that secures vest 110 to the subject's torso. According to the invention, various conventional closure means, such as a hook and pile system, e.g., VELCRO® such as that manufactured by Velcro, Inc., snaps, a zipper, etc., can be incorporated into vest 110 to facilitate closure thereof.

In a preferred embodiment of the invention, closure means 115a includes an integral conventional zipper system. In one embodiment, the zipper system closure means 115a is adapted and positioned to close front panel 112 and rear panel 114 and to secure vest 110 to a subject's body by moving a zipper tab 115b and, hence, engaging the zipper teeth in a downward direction (denoted by Arrow A).

According to the invention, vest 110 can include any material that is suitable for a wearable garment or clothing. In one embodiment, vest 110 includes an elastic material, e.g., a polyurethane-polyurea copolymer such as LYCRA® material made by DuPont, that allows vest 110 to conform to the body shape (i.e. body conforming) when secured thereon.

Figure 14:
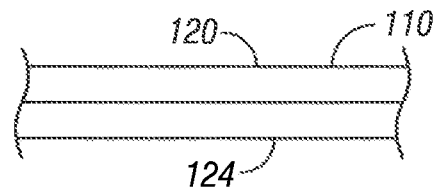
FIG. 14 is a partial side, sectional view of a physiological monitoring garment, showing the top and bottom layers thereof, according to one embodiment of the invention.
Figure 15:
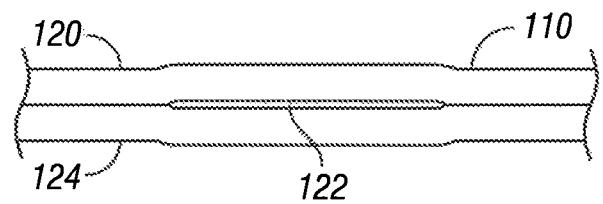
FIG. 15 is a partial side, sectional view of a physiological monitoring garment, showing a pocket formed between the top and bottom layers thereof, according to one embodiment of the invention.

Referring now to FIGS. 14 and 15, in one embodiment vest 110 includes outer layer 120 and inner layer 124, each layer 120, 124 preferably including the same material. Disposed at appropriate anatomical and/or desired positions on vest 100 is at least one garment pocket 122 (preferably a plurality of garment pockets 122).

According to the invention, the pockets 122 can include various shapes and sizes to facilitate receipt and secure positioning of selective monitoring system components, (e.g., magnetometers 22a, 22b, 24a, 24b, physiological sensors, and associated processors control units, etc.).

Pockets 122 can also be formed by various conventional means. In one embodiment, pockets 122 are formed by cutting an opening in one panel (e.g., panel 120 or 124) and forming a closed pocket with the desired size and shape by sewing the border thereof. In one embodiment, pre-formed pockets are sewn on or within vest 110 (e.g., between vest panels 120, 124).

Figure 16:
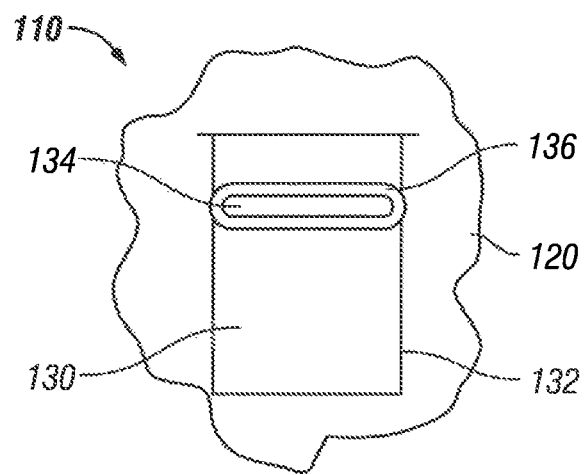
FIG. 16 is a front plan view of a pre-formed garment pocket, according to one embodiment of the invention.

Referring now to FIG. 16, there is shown one embodiment of a pre-formed pocket 130 of the invention. Pocket 130 includes an opening 134 that is disposed, in this instance, proximate the top of pocket 130. In a preferred embodiment, opening 134 is reinforced.

In the illustrated embodiment, pocket 130 is sewn (denoted generally with reference character "132") between vest panels 120, 124. As indicated above, pocket 130 can also be sewn to or on the outer surface of top panel 120 or bottom panel 124.

As indicated above, pockets 122, 130 are configured and adapted to receive and securely position selective monitoring system 10 components, such as, for example, employed magnetometers, processors, control units, etc.

As also indicated above, the magnetometers (e.g., magnetometers 22a, 22b, 24a, 24b), and additional sensors, if employed, can be positioned on or in vest 110 at virtually any desired position, whereby, when vest 110 is worn by a subject the magnetometers and other sensors are positioned proximate any anatomically appropriate or desired position on the subject's body.

To facilitate power transmission to and communication by and between the monitoring system components, vest 110 further includes at least one garment circuit (preferably a plurality of garment circuits) having at least one integral garment conductor associated therewith.

Referring now to FIGS. 17 and 18, there is shown an embodiment of the physiological monitoring garment 110 having a plurality of integral garment conductors associated therewith. As illustrated in FIGS. 17 and 18, in some embodiments of the invention, the garment 110 includes a first plurality of integral conductors or pathways 152. In some embodiments, the first plurality of integral conductors 152 are substantially horizontally disposed. In some embodiments, the first plurality of integral conductors comprise stretchable conductors.

According to the invention, the various electrically conductive materials can be incorporated into garment 110 by, for example, weaving, knitting, or surface application to provide (or construct) the first plurality of integral conductors 152 and, hence, to facilitate connection by and between sensors, such as the magnetometers, and an electronic unit.

According to the invention, the incorporation of these conducting pathways 152 are chosen based on the fabric assembly technique (e.g., knitted or woven). Potential embodiments include silver plated or silver containing threads, and other conductive thread materials, with the exclusion of traditional copper wiring.

In some embodiments of the invention, the garment 110 includes at least one conductive connector (more preferably a plurality of conductive connectors) that facilitates connection by and between sensors and related components disposed on the outer garment layer 120 and the inner garment layer 124. In one embodiment, the connectors include silver plated snap fasteners.

According to the invention, the physiological monitoring garment 110 also includes a central communications pathway (shown in phantom and designated generally with the reference character "154") in communication with the first plurality of integral conductors 152. According to the invention, the central communications pathway 154 can include a ribbon containing fine wires, a series of discrete channels containing strips of metalized or otherwise electrically conductive yarns, thread, or fabric.

In the illustrated embodiment shown in FIGS. 17 and 18, the monitoring system 10 associated with the physiological monitoring garment 110 includes a magnetometer system, (e.g., paired magnetometers 155a, 155b, 155c, 155d, and at least one ECG sensor, not shown). As illustrated in FIGS. 17 and 18, monitoring garment 110 thus includes pockets 133 configured to receive and securely position the paired magnetometers 155a, 155b, 155c, 155d.

Figure 21:
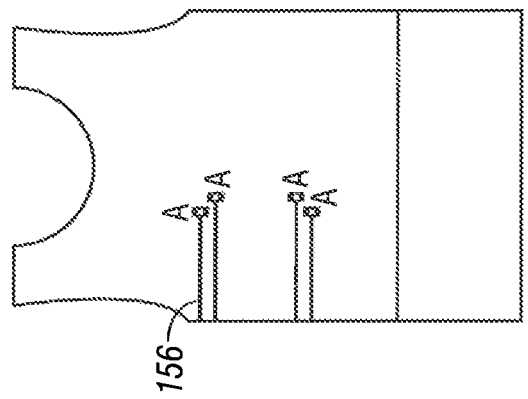
FIG. 21 is a back plan view of the physiological monitoring garment shown in FIG. 19 showing magnetometer circuits, according to one embodiment of the invention.
Figure 20:
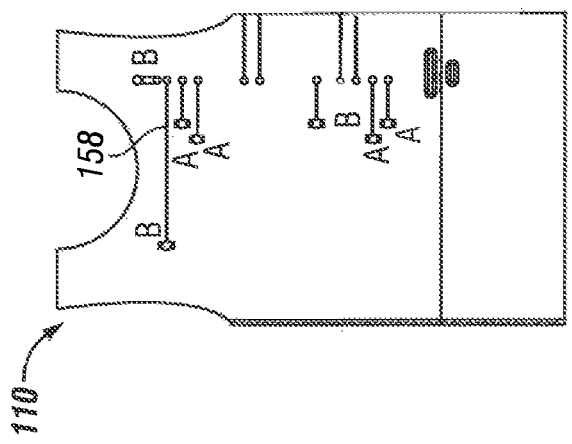
FIG. 20 is a front plan view of the physiological monitoring garment shown in FIG. 19 showing ECG and magnetometer circuits, according to one embodiment of the invention.
Figure 19:
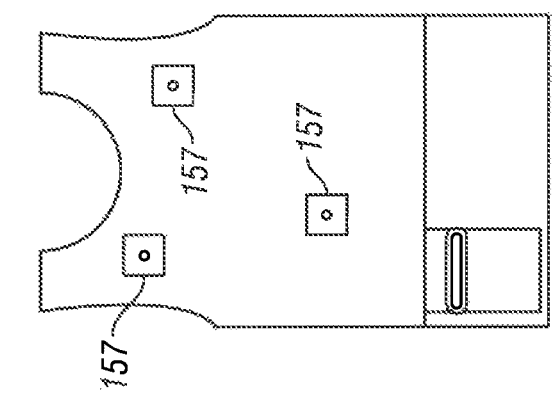
FIG. 19 is a back plan view of a physiological monitoring garment showing incorporated ECG sensor connections, according to one embodiment of the invention.

Referring to FIGS. 19-21, the physiological monitoring garment 110 further includes associated magnetometer circuit 156 and ECG circuit 158. In one embodiment of the invention, magnetometer circuit 156 includes pairs of conductors that are vertically oriented along one side of the shirt and connected to horizontal conductors woven into garment 110. According to the invention, connection between the vertical pairs and horizontal pairs can be effected by stitching with conductive materials, connecting with conductive epoxy, or preferably by standard miniature garment snap fasteners attached to the vertical conductors and to the horizontal conductors by standard crimped-on piercing fasteners.

In one embodiment, similar pairs of vertical and horizontal conductors are employed for magnetometers positioned over the thorax and abdomen area of garment 110.

In one embodiment of the invention, the ECG circuit 158 includes pairs of conductors that are vertically oriented along one side of the shirt and connected to horizontal conductors woven into garment 110. Connection between the vertical pairs and horizontal pairs can similarly be effected by stitching with conductive materials, connecting with conductive epoxy, or preferably by standard miniature garment snap fasteners attached to the vertical conductors and to the horizontal conductors by standard crimped-on piercing fasteners.

Further, in some embodiments, the horizontal conductors are terminated in woven-in conductive patches 157 located proximal to the desired locations for sensing the electrical activity of the heart. The patches 157 can serve directly as the ECG sensors or can be electrically connected to standard adhesive ECG electrodes by, for example, the inclusion of crimped-on snap fasteners within the patches.

Garment Construction

Construction of the monitoring garment of the invention will now be described in detail. It is however to be understood the construction described below is merely one exemplary method of constructing the monitoring garment and is not meant to limit the scope of the invention in any manner.

In one embodiment, garment 110 is constructed by a semi-automated process, wherein a tubular garment section is knitted using conductive and non-conductive threads. The garment section includes horizontal conductive areas knitted into what will become the outer layer of garment 110, conductive patches knitted into the areas that will be ECG electrodes in the inner layer of the garment 110, a separate elastically knitted band that will form the waist-band of garment 110, and a pocket to receive the electronics module.

In a separate operation, a woven ribbon connector is fabricated from metallic conductive threads and non-conductive material. A crimped-on connector is attached to one end, and snap fasteners are attached vertically at break-out points for connection to the knitted horizontal conductors. The tube is folded over on itself to position the inner layer inside the outer layer, arm and neck openings are formed, and the waist-band is sewn on. Snap fasteners are attached to the garment, making connections to the ECG patches from the outside layer conductors, and providing connection points to the vertical ribbon cable.

Pockets for the magnetometers, ribbon cable, and electronics module are formed by processes, such as, for example, sonic welding, stitching, to adhesive. The magnetometers are attached using snap fasteners, and the vertical ribbon is inserted and connected to the knitted conductors by snap fasteners.

As will readily be appreciated by one having ordinary skill in the art, the physiological and performance monitoring garment and associated systems of the invention, described above, provide numerous significant advantages over conventional physiology monitoring methods and systems. Among the advantages is the provision of a physiological monitoring garment that provides accurate, real-time determination of a plurality of physiological characteristics, does not impede mobility, and is simple to manufacture. The physiological monitoring garment is also useful in numerous applications, including ambulatory home and outpatient monitoring, and monitoring subjects during potentially stressful or hazardous situations and athletic and/or competition training.

Additional advantages and applications of the present invention are apparent with reference to the systems and methods disclosed in U.S. patent application Ser. No. 12/869,578, filed Aug. 26, 2010, U.S. patent application Ser. No. 12/869,582, filed Aug. 26, 2010, U.S. patent application Ser. No. 12/869,576, filed Aug. 26, 2010, U.S. patent application Ser. No. 12/869,585, filed Aug. 26, 2010, U.S. patent application Ser. No. 12/869,592, filed Aug. 26, 2010, U.S. patent application Ser. No. 12/869,625, filed Aug. 26, 2010, and U.S. patent application Ser. No. 12/869,586, filed Aug. 26, 2010, each of which is incorporated by reference herein in its entirety.

Without departing from the spirit and scope of this invention, one of ordinary skill can make various changes and modifications to the invention to adapt it to various usages and conditions. As such, these changes and modifications are properly, equitably, and intended to be, within the full range of equivalence of the invention.

What is claimed is:

1. A fitness monitoring system for monitoring physiological parameters of a subject engaged in a physical activity, comprising:

a sensor subsystem including a first sensor and a second sensor, wherein the first sensor comprises a multi-layered printed circuit comprising a conductive circular coil formed from a plurality of printed circuit boards;

a microcontroller; and driver circuitry configured to convert a square wave drive from the microcontroller into an efficient current drive for the coil, wherein each layer of the multi-layered printed circuit comprises a continuous turn of the coil on one of the printed circuit boards, wherein the turns of the coil are connected in series, wherein the first and second sensors are responsive to changes in a parameter, and wherein the sensor subsystem is configured to generate and transmit a signal representative of the parameter.

2. The system of claim 1, wherein:

the conductive circular coil comprises a six-layer printed circuit board having eighteen turns on each layer.

3. The system of claim 2, wherein the coil is approximately two inches in diameter.

4. The system of claim 1, wherein the layers are connected together in series using printed circuit layer connectors.

5. The system of claim 1, further comprising a battery with a voltage range of approximately 2.8V to 3.7V, configured to supply power to the sensor subsystem.

6. The system of claim 1, wherein the driver circuitry is configured to provide monitoring of actual drive signals to the microcontroller.

7. The system of claim 1, further comprising:

a processor subsystem in communication with the sensor subsystem and configured to receive the signal, wherein the processor subsystem is programmed and adapted to control the sensor subsystem and to process the signal, and wherein the processor subsystem includes a relationship for determining a respiratory characteristic from the signal, and wherein the processor subsystem is adapted to generate and transmit a respiratory parameter signal representing the respiratory parameter.

8. The system of claim 1, wherein the first and second sensors are responsive to changes in the distance therebetween, and wherein the signal represents a change in the distance between the first and second sensors.

9. The system of claim 1, further comprising a capacitor network configured to match the square wave drive to a voltage drive requirement of the coil.

10. The system of claim 1, wherein the sensor subsystem includes a device for monitoring the subject's movement.

11. The system of claim 10, wherein the sensor subsystem includes an inertial sensor.

12. The system of claim 10, wherein the sensor subsystem includes a GPS receiver.

13. The system of claim 1, wherein the conductive circular coil comprises a plurality of continuous turns on each layer of the multi-layered printed circuit.

* * * * *